United States Patent
Li et al.

(10) Patent No.: US 10,377,622 B2
(45) Date of Patent: Aug. 13, 2019

(54) REFILLABLE DEVICE

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Changzheng Dai, Shenzhen (CN); Xingbing Zou, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 99 days.

(21) Appl. No.: 15/638,357

(22) Filed: Jun. 29, 2017

(65) Prior Publication Data

US 2017/0297892 A1  Oct. 19, 2017

Related U.S. Application Data

(63) Continuation of application No. 15/268,633, filed on Sep. 18, 2016.

(30) Foreign Application Priority Data

Sep. 30, 2015 (CN) .......................... 2015 1 0635529

(51) Int. Cl.
*B67D 7/02* (2010.01)
*B65D 47/26* (2006.01)
*A24F 1/26* (2006.01)
*A24F 47/00* (2006.01)
*B65B 1/04* (2006.01)
*B67D 7/54* (2010.01)

(52) U.S. Cl.
CPC .............. *B67D 7/0288* (2013.01); *A24F 1/26* (2013.01); *A24F 47/008* (2013.01); *B65B 1/04* (2013.01); *B65D 47/265* (2013.01); *B67D 7/54* (2013.01)

(58) Field of Classification Search
CPC ......... B65B 39/003; B65B 3/06; B65B 39/04; B05B 11/0097; B05B 7/2486; B05B 7/24; B65D 47/24; B65D 47/26; B65D 47/265; B65D 47/00; B65D 3/0032; F16K 15/188; F16L 37/46; B65G 65/4818
USPC .................................. 141/346, 347, 383–386
See application file for complete search history.

(56) References Cited

U.S. PATENT DOCUMENTS

| 4,538,653 A | * | 9/1985 | Shea ..................... F16K 11/074 141/285 |
| 5,947,171 A | * | 9/1999 | Woodruff ............. B65D 23/102 141/346 |
| 8,539,994 B2 | * | 9/2013 | Cuzydlo ............. A61M 16/186 141/346 |

(Continued)

*Primary Examiner* — Timothy L Maust
(74) *Attorney, Agent, or Firm* — Cheng-Ju Chiang

(57) ABSTRACT

The present disclosure relates to a refillable device. The refillable device includes a liquid chamber in the refillable device, a connection end, a sealing component arranged in the connection end, and a rotating mechanism. The liquid chamber is configured for storing tobacco liquid. The connection end is configured for connecting with an open end of a liquid injecting container. The sealing component defines a liquid inlet. The rotating mechanism tightly abuts against the sealing component. The rotating mechanism is rotatable between a first position where the liquid inlet is opened, and a second position where the liquid inlet is sealed.

7 Claims, 10 Drawing Sheets

(56) References Cited

U.S. PATENT DOCUMENTS

| | | | |
|---|---|---|---|
| 8,925,593 B2 * | 1/2015 | Lamboux | A45D 34/02 141/18 |
| 2015/0245654 A1 * | 9/2015 | Memari | A24F 15/12 141/2 |

* cited by examiner

US 10,377,622 B2

REFILLABLE DEVICE

CROSS-REFERENCE OF RELATED APPLICATION

This application is a continuation application of the prior U.S. patent application Ser. No. 15/268,633, filed on Sep. 18, 2016, now published as U.S. Publication No. 2017/0001854A1, the entire content of which is incorporated herein by reference.

TECHNICAL FIELD

The present invention relates to a liquid injecting container, a refillable liquid injecting system/device including same, and a liquid injecting method using same.

BACKGROUND ART

A refillable electronic cigarette is becoming more and more popular because it is environmental-friendly. When tobacco liquid in the refillable electronic cigarette is used up, the user of the electronic cigarette usually uses an injector to fill in tobacco liquid. However, during this process, the tobacco liquid may leak out. For example, since the injector is not fixedly coupled with the electronic cigarette, the tobacco liquid may leak when the electronic cigarette is turned over, thus rendering user experience unsatisfactory.

What are needed, therefore, are a liquid injecting container, a refillable liquid injecting system including same, and a liquid injecting method using same, which can overcome the above shortcomings.

SUMMARY

The present disclosure relates to a liquid injecting container for storing liquid and injecting the liquid into a refillable device. The liquid injecting container includes a hollow shell, a sealing component, and a rotating body. The shell has an open end configured for connecting the refillable device. The sealing component and the rotating body are arranged in the open end. The rotating body is rotatable relative to the sealing component, the sealing component defines at least one liquid outlet, the rotating body is capable of rotating driven by the refillable device between a first position where the rotating body seals the at least one liquid outlet, and a second position where the at least one liquid outlet is opened, such that the liquid in the liquid injecting container can flow into the refillable device.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
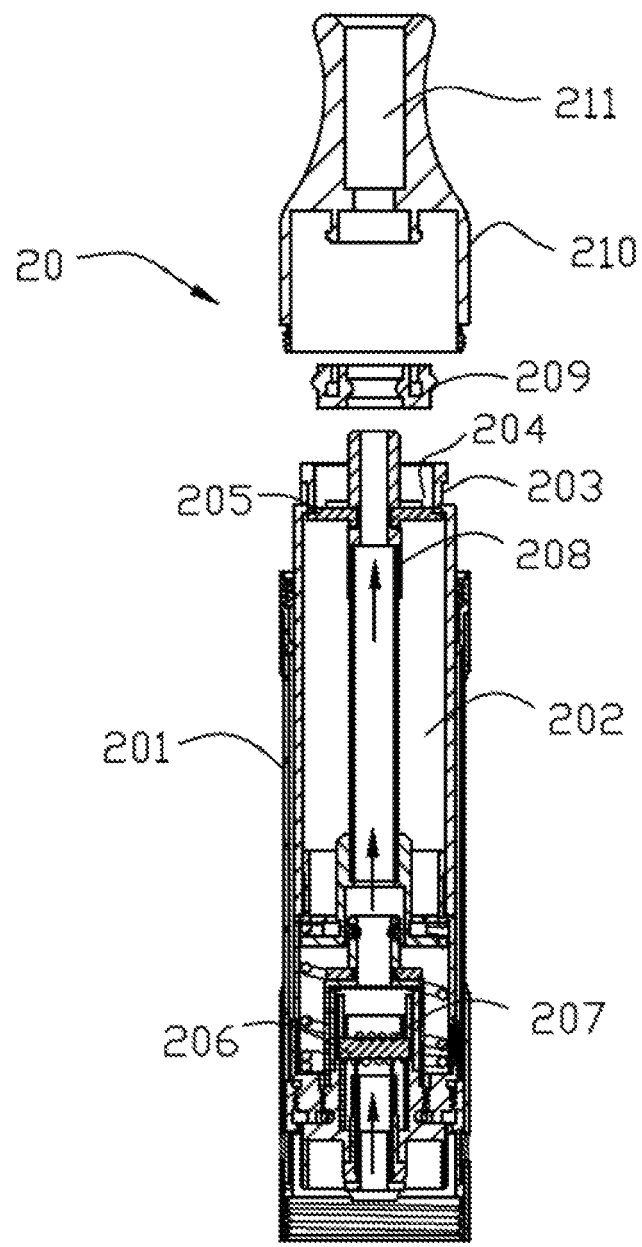
FIG. 1 is a cross-sectional view of a refillable device according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

First Embodiment

Referring to FIG. 1, the present disclosure relates to a refillable liquid injection system. The refillable liquid injection system includes a refillable device 20 (e.g., an atomizer of an electronic cigarette) and a liquid injecting container 10 (Referring to FIG. 3) for storing tobacco liquid therein. The refillable device 20 includes a housing 201 and a liquid chamber 202 formed in the housing 201. The liquid chamber 202 is configured (i.e., structured and arranged) for storing tobacco liquid. An air tube 208 is provided in the liquid chamber 202. An end of the air tube 208 is connected with an air outlet 211 of a mouthpiece 210. The housing 201 includes a connection end 203 for connecting with the liquid injecting container 10. The connection end 203 includes a liquid inlet 204. The mouthpiece 210 and a sealing ring 209 are detachably connected with the connection end 203. In a normal state, the sealing ring 209 is configured for sealing the liquid inlet 204. When the tobacco liquid in the refillable device 20 is used up, only the mouthpiece 210 and the sealing ring 209 are detached, the connection end 203 is connected with the liquid injecting container 10, and then the tobacco liquid is injected into the liquid chamber 202 via the liquid inlet 204.

The above atomizer further includes a liquid conducting body 206 and a heating element 207. The liquid conducting body 206 is configured for absorbing tobacco liquid from the liquid chamber 202. The heating element 207 is configured for heating the tobacco liquid to form aerosol. The aerosol passes through the air pipe 208 and reaches the air outlet 211. The liquid conducting body 206 may be made of glass fiber. In the present embodiment, the heating element 207 is a heating wire wound around the liquid conducting body 206. As seen in FIG. 1, an elastic piece 205 is provided at the connection end 203 to seal the liquid inlet 204. The elastic piece 205 is annular, and nests the air pipe 208. The elastic piece 205 is made of resilient material. In a normal state, the elastic piece 205 seals the liquid inlet 204. When the connection end 203 is connected to a liquid injecting container 10, the liquid injecting container 10 pushes the elastic piece 205 open, so that tobacco liquid can be filled in via the liquid inlet 204. After finishing injection, the liquid injecting container 10 is removed, and then the elastic piece 205 restores to its original shape to seal the liquid inlet 204.

Figure 2:
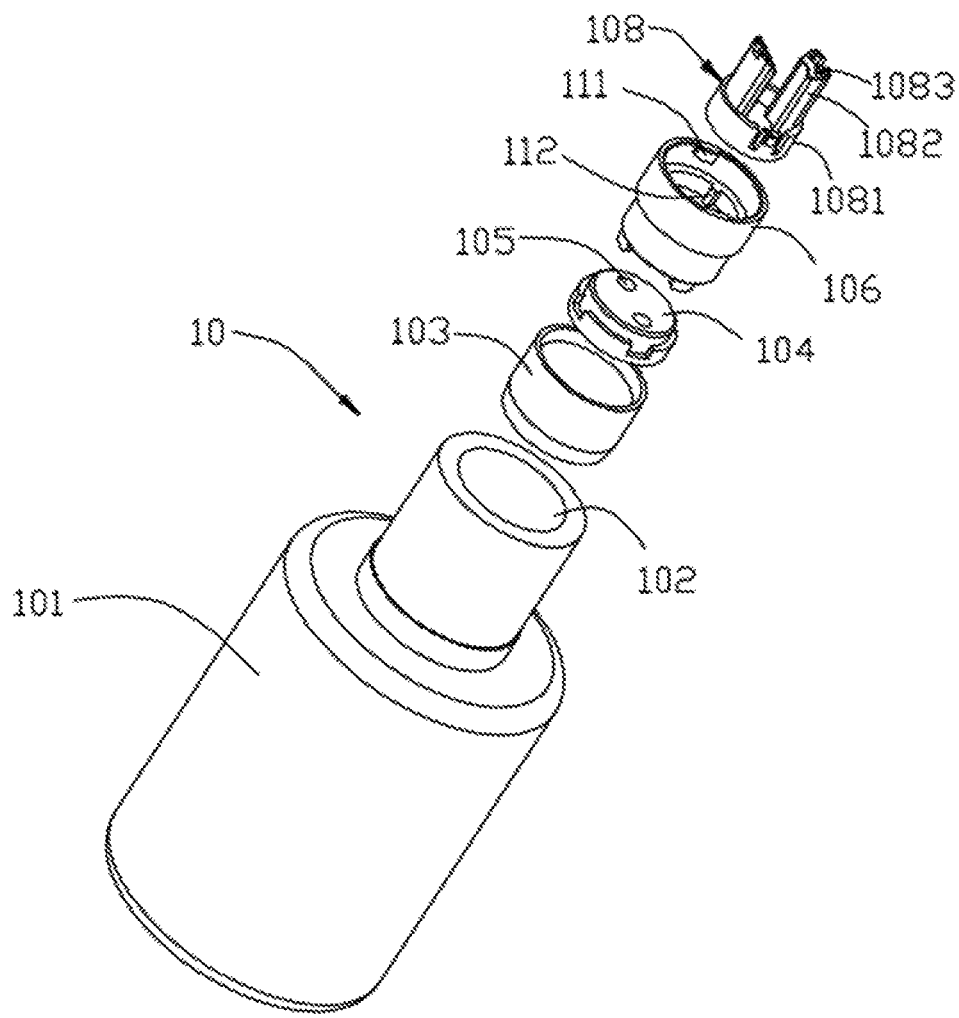
FIG. 2 is an exploded perspective view of a liquid injecting container.
Figure 3:
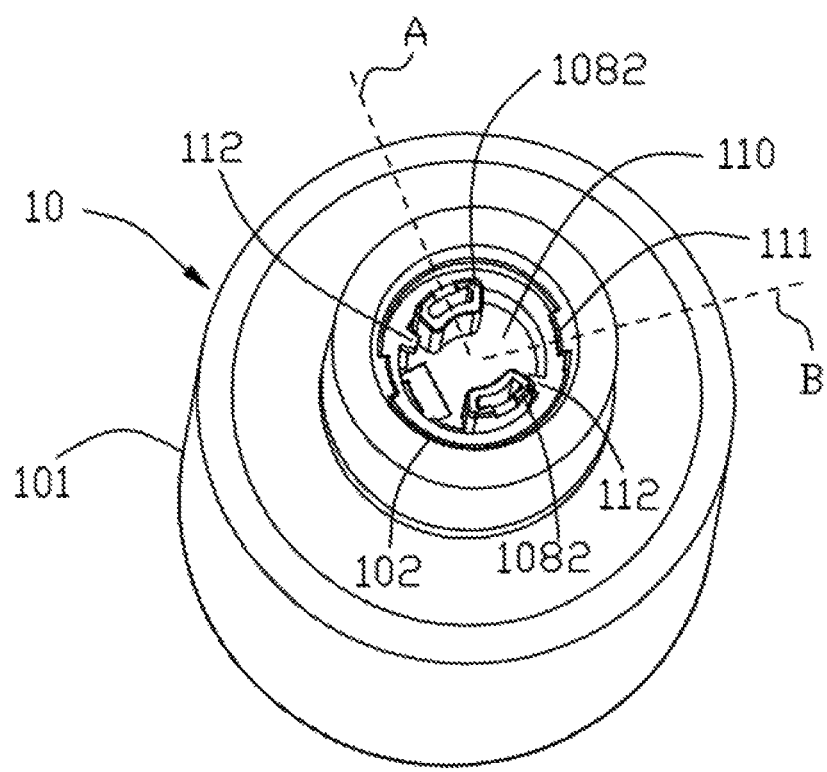
FIG. 3 is a perspective view of a liquid injecting container showing a first position and a second position.

Referring to FIGS. 2-3, the liquid injecting container 10 includes a shell 101. The shell 101 includes an open end 102 configured (i.e., structured and arranged) for connecting the refillable device 20. A sealing component 104 and a rotating body 108 are arranged in the open end 102. The rotating body 108 is rotatable relative to the sealing component 104. The sealing component 104 defines at least one liquid outlet 105. In the present embodiment, the liquid outlet 105 is in the form of two through holes, which are centrally symmetric about a center of the sealing component 104. The rotating body 108 is capable of being driven by the refillable device 20 to rotate between a first position A and a second position B. When the rotating body 108 is in the first position A, the liquid outlet 105 is sealed; when the rotating body 108 is in the second position B, the liquid outlet 105 is opened, so that the tobacco liquid in the liquid injecting container 10 can flow into the liquid chamber 202 of the refillable device 20. For example, an angle formed between the first position A and the second position B is 90 degrees.

A connection holder is arranged in the open end 102, and configured for connecting with the connection end 203. The rotating body 108 and the sealing component 104 are both arranged in the connection holder. In the present embodiment, the connection holder includes a top holder 103 and a bottom holder 106. The top holder 103 and the bottom holder 106 are both fixedly assembled in the open end 102. The sealing component 104 may be made of flexible material, e.g., silicone. The sealing component 104 and the top holder 103 are coupled by interference fit, and non-rotatable relative to each other. An end surface of the rotating body 108 elastically abuts against the sealing component 104, and the rotating body 108 is rotatable relative to the bottom holder 106. A liquid passage is defined in the rotating body 108. During rotation, when the liquid outlet 105 aligns with the liquid passage, liquid in the liquid injecting container 10 can flow out; when the liquid outlet 105 is misaligned with the liquid passage, the liquid cannot flow out. More about the liquid passage will be described below.

Figure 4:
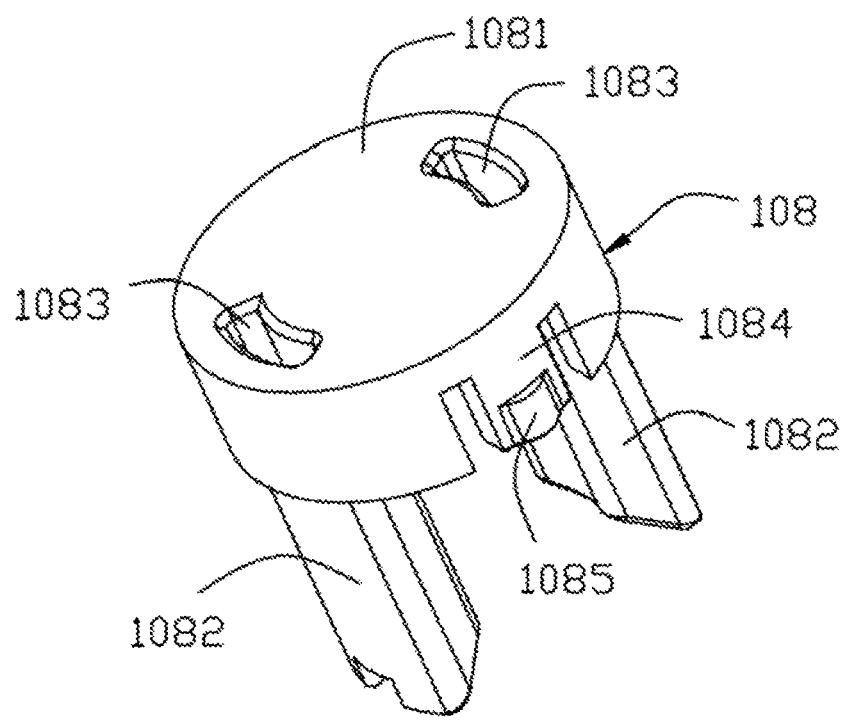
FIG. 4 is an exploded perspective view of a rotating body according to a first embodiment.

Referring to FIG. 4, quite usefully, the rotating body 108 includes a main body 1081 and at least one inserting part 1082 extending from the main body 1081 along a direction of liquid injection. The inserting part 1082 defines a liquid passage 1083, which can function as the above mentioned liquid passage of the rotating body 108. When the refillable device 20 is connected to the liquid injecting container 10, the inserting part 1082 can insert into the refillable device 20 through the liquid inlet 204. In the present embodiment, the rotating body 108 includes two inserting parts 1082. The liquid passage 1083 extends through the main body 1081 and the inserting part 1082. The end surface of the main body 1081 elastically abuts against the sealing component 104. The main body 1081 includes a deformable arm 1084 on a side surface, and the deformable arm 1084 includes a protrusion 1085. The connection holder includes at least two vertical grooves defined in an inner wall. An arc angle between the two vertical grooves is equal to that between the first position A and the second position B. When the rotating body 108 is in the first position A or the second position B, the protrusion 1085 is engaged in one of the vertical grooves.

Referring to FIG. 3, the connection holder includes a restriction part 112 configured for limiting rotation of the rotating body 108. In detail, the bottom holder 106 includes a receiving chamber 110 for receiving the refillable device 20. The receiving chamber 110 includes two protruding restriction parts 112 symmetrically arranged on an inner wall. When the rotating body 108 is in the first position A, the inserting part 1082 is adjacent to one of the restriction parts 112; when the rotating body 108 is rotated clockwise, the other restriction part 112 prevents the inserting part 1082 from further rotating, and restricts the inserting part 1082 in the second position B.

The bottom holder 106 includes a protruding part 111 on an inner wall of the receiving chamber 110. The protruding part 111 is configured for coupling with the connection end 203 to form a snap-fit connection. In the present embodiment, the top holder 106 includes two protruding parts 111 centrally symmetric. After the refillable device 20 is connected with the open end 102 and is rotated a certain angle, the liquid injecting container 10 and the refillable device 20 cooperatively form the snap-fit connection via the protruding part 111, and a liquid path is formed between the liquid injecting container 10 and the refillable device 20. The snap-fit connection ensures that the liquid injecting container 10 and the refillable device 20 are not separated from each other during liquid injection. During rotation, the refillable device 20 drives the rotating body 108 to rotate.

Figure 5:
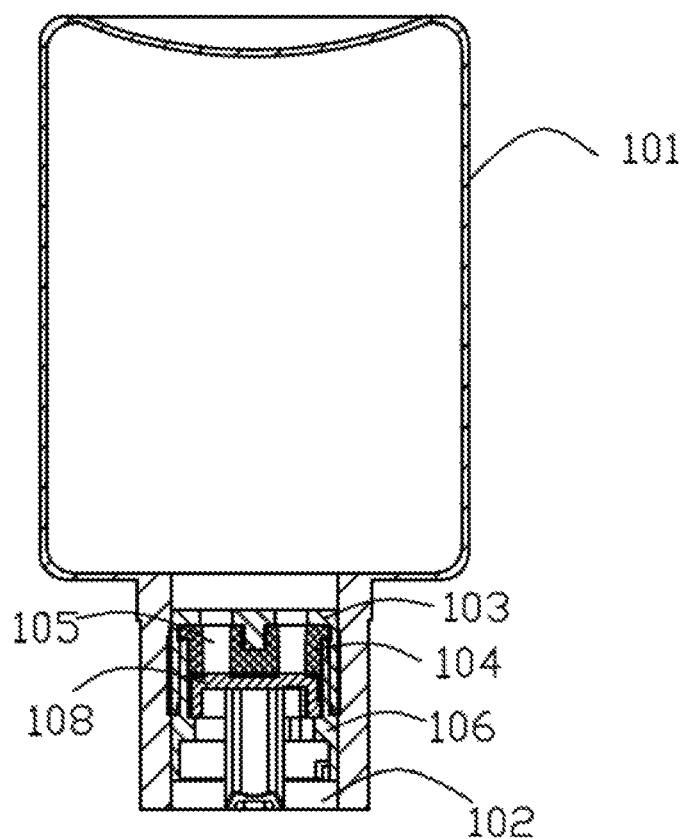
FIG. 5 is a cross-sectional view of the liquid injecting container when liquid outlets are sealed.
Figure 6:
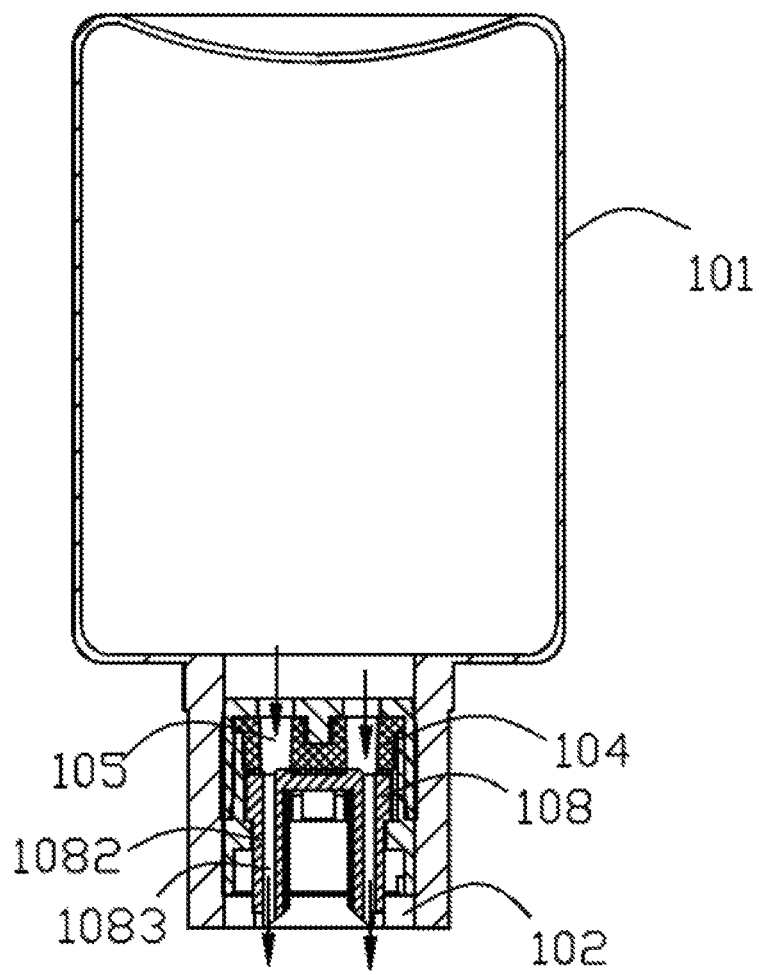
FIG. 6 is a cross-sectional view of the liquid injecting container when liquid outlets are opened.

Referring to FIG. 5, the rotating body 108 is in the first position A, the main body 1081 of the rotating body 108 seals the liquid outlet 105. Referring to FIG. 6, the rotating body 108 is rotated to the second position B, the liquid passage 1083 in the rotating body 108 is in communication with the liquid outlet 105. Quite usefully, to inject tobacco liquid fast, the shell 101 of the liquid injecting container 10 is made of deformable material, e.g., flexible plastic. When the shell 101 is compressed, the tobacco liquid is expelled from the liquid outlet 105. It is to be understood that the tobacco liquid can also flow into the refillable device 20 naturally due to gravity.

Figure 7:
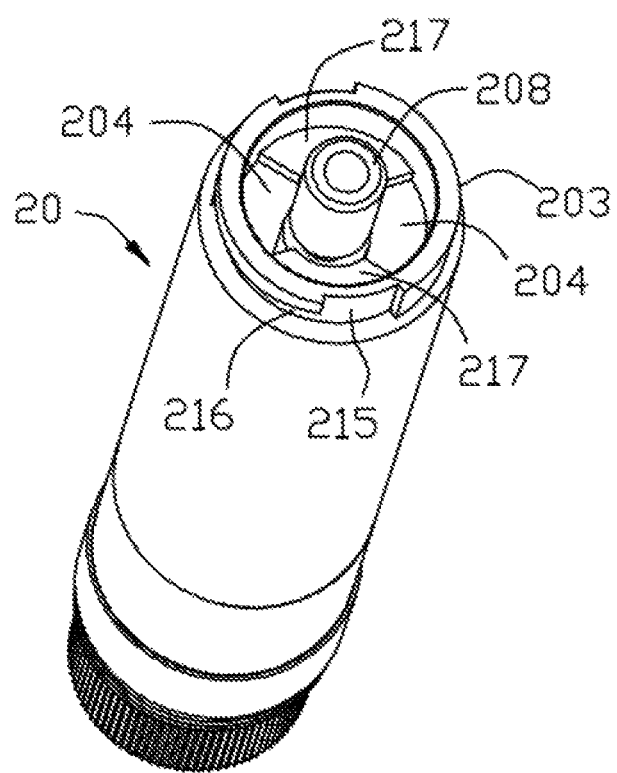
FIG. 7 is a perspective view showing a connection end of the refillable device.
Figure 8:
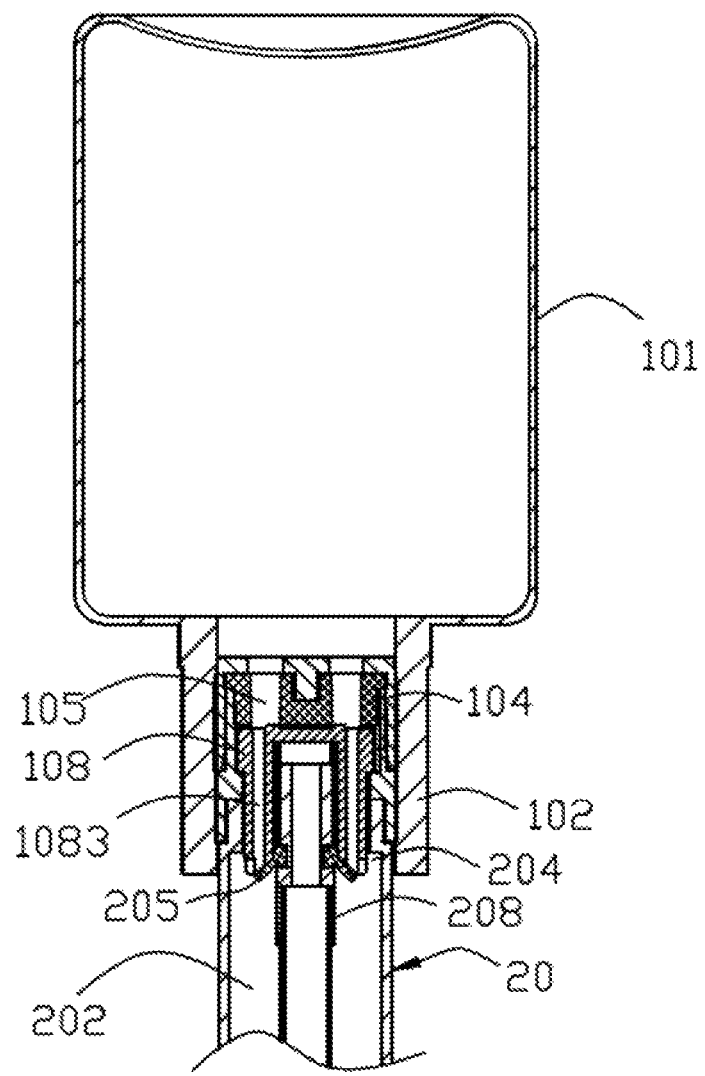
FIG. 8 is a cross-sectional view of a refillable liquid injecting system, including the liquid injecting container and the refillable device.

Referring to FIGS. 7 and 8, the refillable liquid injecting system includes the liquid injecting container 10 and the refillable device 20 (the mouthpiece 210 and the housing 201 are omitted from FIG. 7). The refillable device 20 includes an engaging part 217 at the connection end 203. The engaging part 217 is configured for coupling with the rotating body 108. When the liquid injecting container 10 is connected to the connection end 203, and is rotated relative to the refillable device 20, the engaging part 217 drives the rotating body 108 to rotate between the first position A and the second position B, thus opening or sealing the liquid outlet 105. In the present embodiment, the refillable device 20 includes two engaging parts 217 symmetric about a central axis of the refillable device 20, and each engaging part 217 is an annular sector. Gaps formed between the two engaging parts 217 serve as the above liquid inlets 204. The engaging parts 217 and a housing of the connection end 203 are integrally formed. When the connection end 203 inserts the open end 102 of the liquid injecting container 10, the two inserting parts 1082 of the rotating body 108 insert the two liquid inlets 204. When the liquid injecting container 10 or the refillable device 20 is rotated, the engaging parts 217 drive the rotating body 108 to rotate.

In the present embodiment, the connection end 203 of the refillable device 20 is inserted into the open end 102 of the liquid injecting container 10, and is rotated a predetermined angle to achieve the snap-fit connection. In detail, the connection end 203 defines arc-shaped grooves 216 in an outer surface configured for coupling with the liquid injecting container 10. The outer surface of the connection end 203 further defines a vertical plug opening 215 matching with the protruding part 111 of the liquid injecting container 10. The protruding part 111 is capable of being inserted into the plug opening 215 and being rotated into the arc-shaped grooves 216. When the liquid injecting container 10 is rotated in place, the liquid injecting container 10 and the connection end 203 form the snap-fit connection, and the engaging parts 217 drive the rotating body 108 to rotate to the second position B, where the liquid outlet 105 is opened. It is to be understood that an arc angle of the arc-shaped groove 216 is substantially equal to an included angle formed between the first position A and the second position B.

Steps of liquid injecting tobacco liquid will be described below. First, the connection end 203 of the refillable device 20 is coupled to the open end 102 of the liquid injecting container 10, the inserting parts 1082 insert into the liquid inlets 204, and push the elastic piece 205 open. In this state, the rotating body 108 is in the original first position A. Then the liquid injecting container 10 is rotated a certain angle to form the snap-fit connection. Subsequently, the engaging parts 217 drive the rotating body 108 to rotate to the second position B. In this position, the liquid outlets 105 are opened, so that a liquid path is established between the liquid outlets 105 and the liquid inlets 204, as seen in FIG. 8. After finishing liquid injection, the liquid injecting container 10 is rotated in a reverse direction, the protruding parts 111 are rotated out from the arc-shaped grooves 216, the engaging parts 217 drive the rotating body 108 from the second position B to the first position A, and the liquid outlets 105 are sealed again. The refillable device 20 is separated from the liquid injecting container 10. During the whole process, the tobacco liquid in the liquid injecting container 10 and the refillable device 20 will not leak.

Quite usefully, referring to FIG. 8, when the liquid outlet 105 is opened, the tobacco liquid can be injected into the liquid chamber 202 quickly by squeezing the shell 101 of the liquid injecting container 10. When the tobacco liquid flows into the liquid chamber 202, air in the liquid chamber 202 is expelled from an air gap between the open end 102 and the connection end 203.

Second Embodiment

Figure 9:
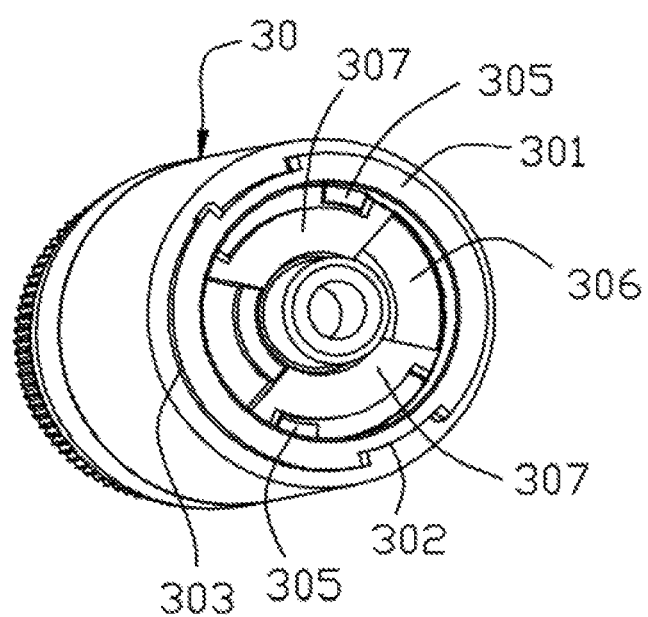
FIG. 9 is a perspective view showing a connection end of the refillable device according to the second embodiment.
Figure 10:
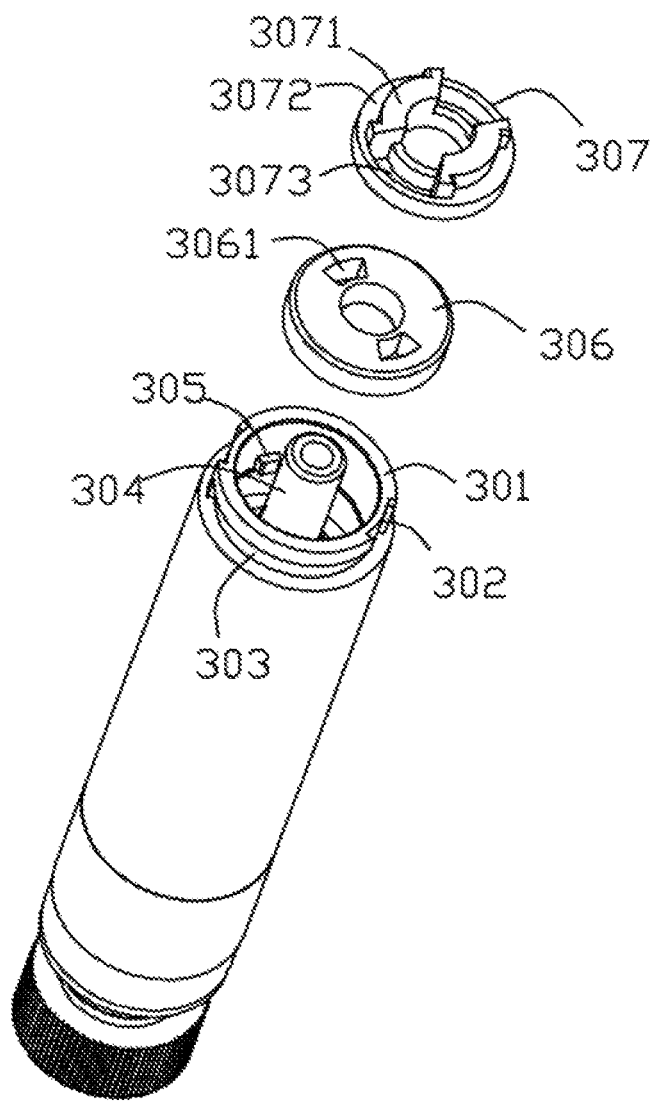
FIG. 10 is an exploded perspective view of the refillable device, omitting a mouthpiece.

Compared with the refillable liquid injecting system according to the first embodiment, a structure of the liquid injecting container in accordance with the present embodiment is identical with that of the first embodiment, and a structure of the connection end 301 (Referring to FIGS. 9-10 of the refillable device 30 is different from that of the first embodiment.

Referring to FIGS. 9-10, a refillable device 30 according to another embodiment is shown. The refillable device 30 includes a connection end 301 at an end. Similar to that in the first embodiment, the connection end 301 defines a vertical plug groove 302 and an arc-shaped groove 303, but an arc angle of the arc-shaped groove 303 is larger than that in the first embodiment. The connection end 301 includes a sealing component 306 and a rotating mechanism 307 tightly and elastically abutting the sealing component 306. The sealing component 306 is made of elastic material, for example, silicone. The sealing component 306 is fixedly engaged in the connection end 301 by interference fit, and nests an air pipe 304. The rotating mechanism 307 also sleeves the air pipe 304, and is rotatable a certain angle relative to the connection end 301. Liquid inlets 3061 are defined in the sealing component 306. The liquid injecting container 10 is capable of driving the rotating mechanism 307 to open or seal the liquid inlets 3061, when the liquid injecting container 10 rotates relative to the refillable device 30.

The rotating mechanism 307 includes two symmetric engaging parts 3071. The two engaging parts 3071 form gaps 3073. The gaps 3073 extend through the rotating mechanism 307. The engaging parts 3071 further define arc-shaped sliding grooves 3072. The connection end 301 further includes limiting blocks 305 formed on an inner wall. The limiting blocks 305 are configured for limiting the rotating mechanism 307 to rotate in a certain angle. The limiting blocks 305 are capable of sliding along the sliding grooves 3072, thus restricting a rotating angle of the rotating mechanism 307.

Quite usefully, the liquid inlets 3061 are two annular sector-shaped through holes. The two through holes are symmetric about a central axis of the refillable device 30. Different from the first embodiment, the engaging parts 3071 are not fixed. Accordingly, when the connection end 301 is inserted into the liquid injecting container 10, the inserting parts 1082 pass through the gaps 3073 and abut against an end surface of the sealing component 306. In this position, the liquid passage 1083 in the inserting parts 1082 is misaligned with the liquid inlets 3061.

In the present embodiment, the rotating mechanism 307 is assembled looser than the rotating body 108, and thus a rotation resistance of the rotating mechanism 307 is less than that of the rotating body 108. Accordingly, when the liquid injecting container 10 is rotated a predetermined angle along the arc-shaped grooves 303, the inserting parts 1082 first drive the rotating mechanism 307 to rotate, the liquid inlets 3061 are exposed and aligned with the liquid passage 1083. In this position, the limiting block 305 slides from an end of the sliding groove 3072 to the other end until the engaging parts 3071 is restricted. If the liquid injecting container 10 is further rotated along the arc-shaped groove 303, the engaging parts 3071 and the connection end 301 together drive the inserting parts 1082 of the rotating body 108 to rotate, so that the liquid outlet 105 is opened. When the liquid injecting container 10 is rotated to an end of the arc-shaped grooves 303 to form a snap-fit connection, the liquid outlet 105 aligns with the liquid passage 1083 and the liquid inlet 3061, thus establishing a liquid path. It is to be understood that an arc angle of the arc-shaped groove 303 is substantially equal to a sum of rotated angles of the rotating mechanism 307 and the rotating body 108. Other structures of the refillable device 30 are substantially identical with that of the refillable device 20 of the first embodiment, and will not be described in detail.

Steps of liquid injecting tobacco liquid of the refillable liquid injecting system are similar to that in accordance with the first embodiment. Differences will be described in detail below. The liquid inlet 3061 in the refillable device 30 is sealed in advance by the rotating mechanism 307, when the liquid injecting container 10 is connected with the refillable device 30, the liquid injecting container 10 is first rotated a first angle, so that the liquid inlet 3061 in the refillable device 30 is opened. Then the liquid injecting container 10 is further rotated a second angle, such that the liquid outlet 105 in the liquid injecting container 10 is opened. When liquid injecting container 10 is rotated in a reverse direction to detach from the refillable device 30, the liquid inlets 3061 are first closed, and then the liquid outlets 105 are closed, thus avoiding liquid leakage. It is to be noted that in other embodiments, the rotating body 108 may be rotated prior to the rotating mechanism 307, that is, the liquid outlets 105 are first opened, and then the liquid inlets 3061 are opened.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A refillable device, comprising:
    a liquid chamber in the refillable device, the liquid chamber being configured for storing tobacco liquid;
    a connection end configured for connecting with an open end of a liquid injecting container;
    a sealing component arranged in the connection end, the sealing component defining a liquid inlet; and
    a rotating mechanism tightly abutting against the sealing component;
    wherein the rotating mechanism is rotatable between a first position where the liquid inlet is opened, and a second position where the liquid inlet is sealed;
    wherein the rotating mechanism comprises two symmetric engaging parts, the two engaging parts cooperatively form two gaps therebetween, and the two gaps extend through the rotating mechanism.

2. The refillable device according to claim 1, wherein the connection end is configured for coupling with the open end of the liquid injecting container via a snap-fit connection.

3. The refillable device according to claim 2, wherein the connection end defines an arc-shaped groove in an outer surface configured for coupling with the liquid injecting container via a snap-fit connection.

4. A refillable device, comprising:
    a liquid chamber in the refillable device, the liquid chamber being configured for storing tobacco liquid;
    a connection end configured for connecting with an open end of a liquid injecting container;
    a sealing component arranged in the connection end, the sealing component defining a liquid inlet;
    a rotating mechanism tightly abutting against the sealing component; and
    an elastic piece arranged in the connection end, wherein the elastic piece is configured for sealing the liquid inlet, and is deformable to open the liquid inlet when pushed by the liquid injecting container;
    wherein the rotating mechanism is rotatable between a first position where the liquid inlet is opened, and a second position where the liquid inlet is sealed.

5. The refillable device according to claim 1, wherein the liquid inlet comprises two annular sector-shaped through holes, and the two through holes are symmetric about a central axis of the refillable device.

6. The refillable device according to claim 1, further comprising a limiting block formed on an inner wall of the connection end, wherein the limiting block is configured for limiting the rotating mechanism to rotate in a certain angle.

7. A refillable device, comprising:
    a liquid chamber in the refillable device, the liquid chamber being configured for storing tobacco liquid;
    a connection end configured for connecting with an open end of a liquid injecting container;
    a sealing component arranged in the connection end, the sealing component defining a liquid inlet;
    a rotating mechanism tightly abutting against the sealing component; and
    a liquid conducting body and a heating element, wherein the liquid conducting body is configured for absorbing the tobacco liquid from the liquid chamber, and the heating element is configured for heating the tobacco liquid absorbed in the liquid conducting body to form aerosol;
    wherein the rotating mechanism is rotatable between a first position where the liquid inlet is opened, and a second position where the liquid inlet is sealed.

* * * * *